United States Patent
Klinec

(10) Patent No.: US 9,470,674 B2
(45) Date of Patent: Oct. 18, 2016

(54) METHOD AND APPARATUS FOR DETECTING CLOTS IN A LIQUID USING MEASURED LIGHT INTENSITY

(71) Applicant: Roche Diagnostics Operations, Inc., Indianapolis, IN (US)

(72) Inventor: Darko Klinec, Calw (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 110 days.

(21) Appl. No.: 14/174,964

(22) Filed: Feb. 7, 2014

(65) Prior Publication Data

US 2014/0231680 A1  Aug. 21, 2014

(30) Foreign Application Priority Data

Feb. 21, 2013  (EP) .................................. 13156233

(51) Int. Cl.
| | |
|---|---|
| *G01N 33/49* | (2006.01) |
| *G01N 21/25* | (2006.01) |
| *G01N 21/31* | (2006.01) |
| *G01N 21/51* | (2006.01) |
| *G01N 35/10* | (2006.01) |
| *G01N 15/06* | (2006.01) |
| *G01N 35/02* | (2006.01) |
| *G01N 21/13* | (2006.01) |
| *G01N 15/04* | (2006.01) |
| *G01N 35/04* | (2006.01) |

(52) U.S. Cl.
CPC ............ *G01N 33/491* (2013.01); *G01N 15/06* (2013.01); *G01N 21/253* (2013.01); *G01N 21/3151* (2013.01); *G01N 21/51* (2013.01); *G01N 35/02* (2013.01); *G01N 35/1016* (2013.01); *G01N 21/13* (2013.01); *G01N 2015/045* (2013.01); *G01N 2015/0693* (2013.01); *G01N 2035/0406* (2013.01); *G01N 2035/1018* (2013.01); *G01N 2201/066* (2013.01); *G01N 2201/0662* (2013.01); *G01N 2201/0668* (2013.01)

(58) Field of Classification Search
CPC .............. G01N 15/06; G01N 121/13; G01N 121/253; G01N 121/3151; G01N 121/51; G01N 133/491; G01N 135/02; G01N 135/1016
See application file for complete search history.

(56) References Cited

U.S. PATENT DOCUMENTS

| | | |
|---|---|---|
| 3,969,079 A | 7/1976 | Catarious et al. |
| 4,876,069 A | 10/1989 | Jochimsen |
| 5,166,889 A | 11/1992 | Cloyd |
| 5,540,081 A | 7/1996 | Takeda et al. |
| 6,706,536 B1 | 3/2004 | Carroll et al. |

(Continued)

FOREIGN PATENT DOCUMENTS

| | | |
|---|---|---|
| CN | 1693884 A | 11/2005 |
| JP | 55-10916 A | 1/1980 |

(Continued)

*Primary Examiner* — Francis M Legasse, Jr.
(74) *Attorney, Agent, or Firm* — Roche Diagnostics Operations, Inc.

(57) ABSTRACT

A method for detecting clots in a liquid is presented. The liquid is in a sample container. Light is irradiated having a first wavelength to the sample container by a first light source at a changeable vertical irradiating position ($P\_0$ to $P\_n$) such that the light irradiated by the first light source passes through the sample container along a first measurement path. An intensity of light having the first wavelength passing along the first measurement path and exiting the sample container is measured. Clots are detected in response to the measured intensity.

14 Claims, 3 Drawing Sheets

(56) References Cited

U.S. PATENT DOCUMENTS

| | | | |
|---|---|---|---|
| 7,227,622 B2* | 6/2007 | Itoh | G01N 33/48 356/39 |
| 2005/0163354 A1 | 7/2005 | Ziegler | |
| 2005/0180884 A1* | 8/2005 | Itoh | G01N 21/59 422/63 |
| 2012/0013889 A1 | 1/2012 | Heise | |

FOREIGN PATENT DOCUMENTS

| | | |
|---|---|---|
| JP | 4-130248 A | 5/1992 |
| JP | 2001-165752 A | 6/2001 |
| JP | 2004-061140 A | 2/2004 |
| JP | 2005-265813 A | 9/2005 |
| JP | 2007-309888 A | 11/2007 |
| JP | 2011-252804 A | 12/2011 |

* cited by examiner

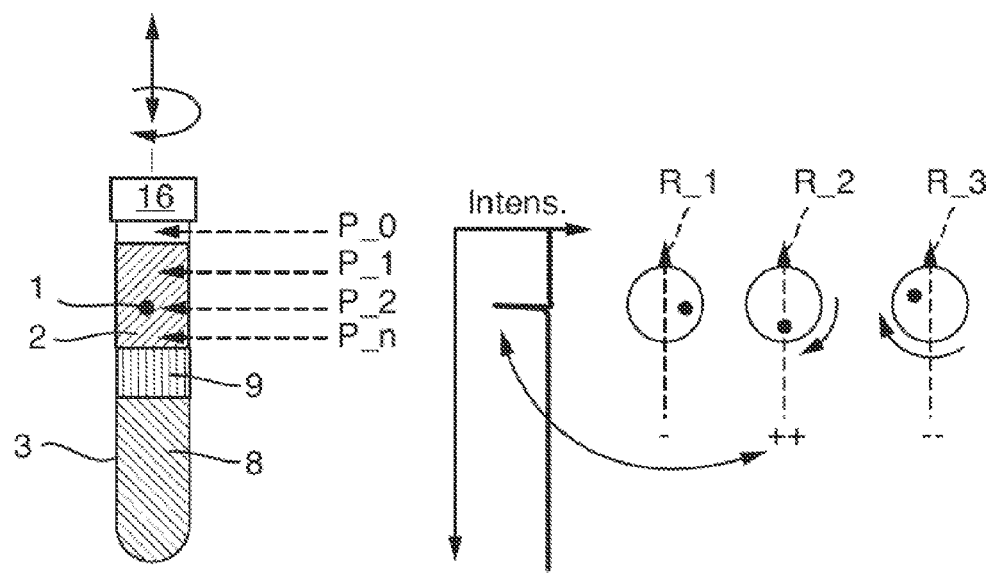
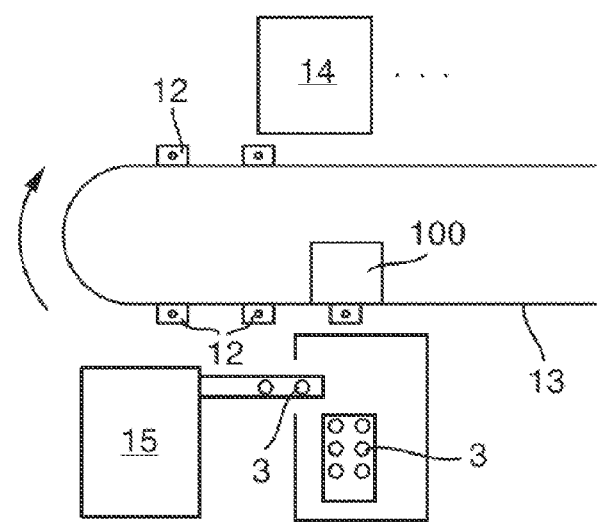

METHOD AND APPARATUS FOR DETECTING CLOTS IN A LIQUID USING MEASURED LIGHT INTENSITY

CROSS-REFERENCE TO RELATED APPLICATIONS

This application is a continuation of EP 13156233.2, filed Feb. 21, 2013, which is hereby incorporated by reference.

BACKGROUND

The present disclosure relates to a method and an apparatus for detecting clots in a liquid contained in a sample container and a laboratory automation system comprising the apparatus In the technical field of laboratory automation, sample containers comprising centrifuged blood samples may have to be processed. The blood samples may be separated into serum and cruor (blood cells) by a separating medium. If, for example, an aliquot of the serum has to be generated, part of the serum has to be transferred to another sample container, for example by a pipette device. If clots are present in the serum, the pipette device may not function properly since clots may block or close an opening of the pipette device. In a prior art pipetting apparatus with clot detection, clot detection is based on measuring pressure difference using pressure sensors.

Therefore, there is a need to provide for a method and an apparatus for reliably detecting clots in a liquid and a corresponding laboratory automation system at a low cost.

SUMMARY

According to the present disclosure, a method for detecting clots in serum is presented. The serum can be in a sample container. The sample container can comprise a centrifuged blood sample. The blood sample can be separated into the serum and at least one other component. The method can comprise irradiating light having a first wavelength to the sample container by a first light source at a vertical irradiating position such that the light irradiated by the first light source can pass through the sample container along a first measurement path. An intensity of light having the first wavelength passing along the first measurement path and exiting the sample container can be measured. The sample container can be moved relative to the first light source without changing the vertical irradiating position such that the light irradiated by the first light source can pass through the sample container along a second measurement path being different from the first measurement path. An intensity of light having the first wavelength passing along the second measurement path and exiting the sample container can be measured. Clots can be detected in response to the measured intensity corresponding to the first measurement path and the measured intensity corresponding to the second measurement path.

Accordingly, it is a feature of the embodiments of the present disclosure to provide for a method and an apparatus for reliably detecting clots in a liquid and a corresponding laboratory automation system at a low cost. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 2 illustrates schematically a method for detecting clots in a liquid using the apparatus depicted in FIG. 1 according to an embodiment of the present disclosure.

FIG. 3 illustrates schematically a laboratory automation system comprising the apparatus depicted in FIG. 1 according to an embodiment of the present disclosure.

DETAILED DESCRIPTION

Figure 1:
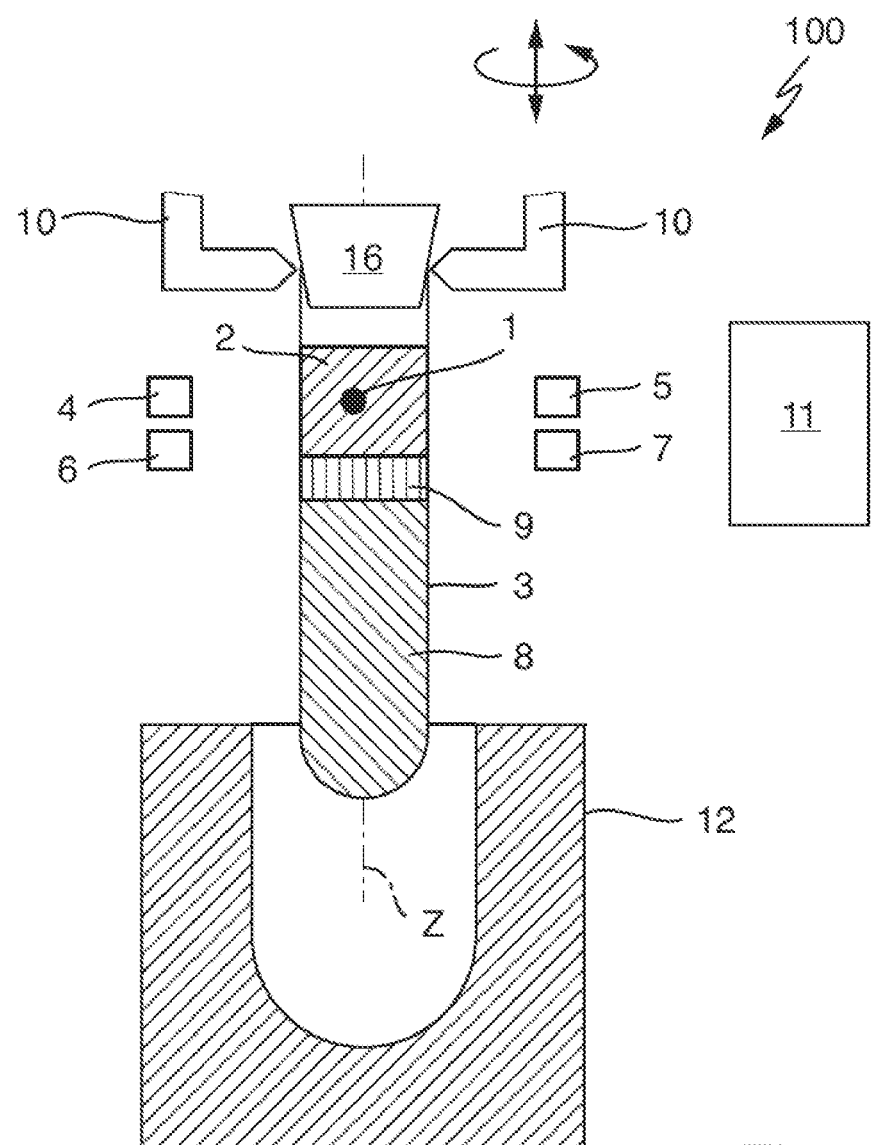
FIG. 1 illustrates schematically an apparatus for detecting clots in a liquid, the liquid being in a sample container according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The method can detect clots in a liquid. The liquid can be in a conventional sample container. A clot can typically comprise afibrinogenaemia fibers, coagulum, fat/protein agglutination or the like.

The sample container can comprise a centrifuged blood sample. The blood sample can be separated into serum (or plasma) and other components such as, for example, cruor (blood cells) and a separating medium (gel). The serum or plasma may be the liquid. The serum or plasma, the separating medium and the cruor may be comprised in the sample container as horizontally separated layers. The content of sample container may be reagent free. In other words, during and before clot detection, no reagent, especially no reagent causing coagulation, may be added to the content of the sample container.

Light having a first wavelength can be irradiated or projected onto the sample container from a first light source. The light source may, for example, be a laser diode. The light emitted by the laser diode may be collimated by a conventional collimator such the light can be emitted in form of a beam having a defined diameter and direction in space.

The sample container may be a conventional cylindrical sample tube as used in laboratory automation. The sample container or tube may have a substantially round cross section (view from top).

The light may be emitted perpendicular to a vertical axis of the sample container at a changeable vertical irradiating position or vertical projecting position such that the light passes through the sample container along a first measurement path. The first measurement path also can be perpendicular to the vertical axis. Perpendicular can mean an angle ranging between about 85 degrees and about 95 degrees, such as between about 89 degrees and about 91 degrees. Further, the first measurement path may intersect the vertical axis of the sample container, that is, go through the center of the sample container.

Next, an intensity of light originating from the first light source, passing along the first measurement path and exiting the sample container can be measured. In other words, the transmission of light having the first wavelength can be measured along the first measurement path.

Light having the first wavelength can be substantially transmitted by serum, plasma, a separating medium and a material of the sample container, but can be substantially blocked or absorbed by the clot, so that if a clot is located on the first measurement path the corresponding measured intensity can decrease significantly or may be even close to zero.

The sample container can be moved relative to the first light source without changing the vertical irradiating position such that the light irradiated by the first light source can pass through the sample container along a second measurement path being different from the first measurement path. The second measurement path may also be perpendicular to the vertical axis of the sample container. Further, the second measurement path may intersect the vertical axis of the sample container, that is, go through the center of the sample container.

Light having the first wavelength generated by the first light source can be irradiated to the sample container perpendicular to the vertical axis of the sample container such that the light passes along the second measurement path.

An intensity of light passing through the second measurement path and exiting the sample container can be measured. In other words, the transmission of light having the first wavelength can be measured along the second measurement path.

A clot, if any, can be detected in response to the measured intensity corresponding to the first measurement path and the measured intensity corresponding to the second measurement path.

The clot, if any, may be detected for a given vertical irradiating position if the measured intensity of the first measurement path differs from the measured intensity of the second measurement path by more than a given quantity.

In order to move the sample container relative to the first light source, the sample container may be rotated around the vertical axis of the sample container. Alternatively or additionally, the first light source may be rotated around the vertical axis of the sample container.

The vertical irradiating position may be changed, for example, to gather further measured intensities corresponding to different vertical irradiating positions. This may, for example, be done to detect vertical clot boundaries.

Light having a second wavelength may be irradiated to the sample container at different vertical irradiating positions. Vertical irradiating positions corresponding to the first and the second wavelengths may be identical.

An intensity of light having the second wavelength exiting the sample container may be measured at the different vertical irradiating positions and positions of the components or layers, for example, the separating medium, the serum and the cruor, may be calculated in response to the measured intensities corresponding to the second wavelength and the measured intensities corresponding to the first wavelength. The method regarding calculating the positions of the components may be performed as disclosed in U.S. 2012/0013889 A1 which is incorporated by reference.

The calculation of the vertical positions of the components may be done before clot detection. The clot detection may be performed only for a given component, for example, only for serum or plasma.

At least a part of the hardware used for calculating the positions of the separating medium, the serum and the cruor may also be used for clot detection, thereby generating synergies reducing cost, complexity, and the like.

The first wavelength may range from about 400 nm to about 1200 nm. The first wavelength may be chosen such that the light having the first wavelength may pass through the liquid and the separating medium basically without damping. In other words, light having the first wavelength can be substantially transmitted by serum, plasma, a separating medium and a material of the sample container but substantially blocked or absorbed by the clot so that if a clot is located on the first measurement path, the corresponding measured intensity can decrease significantly or may be even close to zero.

The second wavelength may range from about 1300 nm to about 1700 nm. The second wavelength may be chosen such that the light having the second wavelength can basically be absorbed by the liquid but may pass through the separating medium basically without damping. In other words, the second wavelength can be substantially blocked or absorbed by the clot, serum, plasma, and cruor, but can be substantially transmitted by the separating medium and the material of the sample container.

By changing the vertical irradiating position, the sample container may be inserted into a sample container rack or carrier. The clot detection can be simultaneously performed. By performing two tasks, namely clot detection and rack insertion, in parallel, the overall processing time may be reduced.

The apparatus can detect clots in a liquid. The liquid can be in a sample container. The apparatus may perform the method described above.

The apparatus can comprises a first light source, for example, a laser diode including corresponding collimation optics, to irradiate light to the sample container having a first wavelength, for example, substantially perpendicular to a vertical axis of the sample container, at a changeable vertical irradiating position.

The apparatus can further comprise a first measuring unit, for example, a photo diode or photo transistor, to measure an intensity of light having the first wavelength passing along a first measurement path and exiting the sample container.

A computing unit, for example, a microprocessor, can detect a clot in response to the measured intensities.

The apparatus may comprise a driving unit to grip and move the sample container relative to the first light source. The driving unit may, for example, rotate the sample container around the vertical axis of the sample container.

The apparatus may comprise a second light source to irradiate light having a second wavelength to the sample container at different vertical irradiating positions and a corresponding second measuring unit to measure an intensity of light having the second wavelength and exiting the sample container.

The computing unit may calculate vertical positions of components comprised in the sample container, for example, the separating medium, the serum or plasma and the cruor, in response to the measured intensities corresponding to the second wavelength and the measured intensities corresponding to the first wavelength.

A laboratory automation system can process components comprised in a sample container.

The system can include the apparatus as described above. The system can further include at least one laboratory station coupled to the apparatus. The system may include different laboratory stations, such as pre-analytical stations, analytical stations and post-analytical stations.

The apparatus and the laboratory station(s) may be coupled by a data bus enabling data exchange between the apparatus and the laboratory station(s).

The laboratory station can operate in response to the clot detection. The laboratory stations may be an aliquoter unit having a pipetting unit. The pipetting unit can have a tip. During aliquoting, the aliquoter unit can control a vertical position of the tip in response to a detected vertical position of at least one interface between different components such that only a desired component can be transmitted into secondary tubes. Further, the aliquoter unit can control aliquoting in response to the clot detection result provided by the apparatus for detecting clots. If a clot is detected, the aliquoter unit may, for example, control the vertical and/or horizontal position of the tip such that the tip may not be blocked or absorbed by the clot. Alternatively, a sample container including clot (or a given number of clots and/or a clot having a dimension bigger than a threshold) may be omitted from further processing.

The system may further include a sample container transport unit to transport sample containers between different laboratory stations. The sample container transport unit can comprise a number, for example, about 10 to about 200, of sample container carriers. The driving unit can insert a sample container into a sample container carrier parallel to clot detection thus increasing the overall processing performance.

The sample container transport unit may include a conveyor (belt). The sample container carriers can be attached to the conveyor.

Referring initially to FIG. 1, FIG. 1 schematically depicts an apparatus 100 for detecting clots 1 in a liquid in form of (blood) serum 2. A transparent sample container 3 can comprise a centrifuged blood sample. The blood sample can be separated into serum 2 and cruor 8 by a separating medium 9. The serum 2, the separating medium 9 and the cruor 8 can be comprised in the sample container 3 as different horizontally separated layers. The content of the sample container 3 can be reagent free, that is, during and before clot detection no reagent, especially no reagent causing coagulation, may be added to the content of the sample container 3. The sample container 3 can be closed by a removable cap 16.

The apparatus 100 can comprise a first light source in the form of a laser diode 4 emitting light having a first wavelength of about 800 nm and corresponding collimation optics (not shown). Opposite to the laser diode 4 at an identical vertical level, a first measuring unit in the form of a photo diode 5 (and corresponding analog and digital circuitry, not shown) can be arranged. The photo diode 5 can measure an intensity of light being emitted by the laser diode 4 and travelling along a measurement path through the sample container 3.

The apparatus 100 can further comprise a second light source in the form of a laser diode 6 emitting light having a second wavelength of about 1550 nm and corresponding collimation optics (not shown). Opposite to the laser diode 6 at an identical vertical level, a second measuring unit in the form of a photo diode 7 can be arranged. The photo diode 7 can measure an intensity of light being emitted by the laser diode 6 and travelling along a measurement path through the sample container 3.

The apparatus 100 can further comprise a driving unit in the form of a pick-and-place unit 10, for example, for vertically moving the sample container 3 relative to the laser diodes 4 and 6 and the photo diodes 5 and 7. The pick-and-place unit 10 can rotate the sample container 3 around a vertical axis Z of the cylindrical sample container 3.

A computing unit in the form of a microprocessor 11, for example, can be coupled to the laser diodes 4 and 6, the photo diodes 5 and 7 and the pick-and-place unit 10. The microprocessor 11 may control the laser diodes 4 and 6 to continuously emit light or to emit light only at discrete vertical positions. The microprocessor 11 may further control the laser diodes 4 and 6 to generate light pulses.

The microprocessor 11 can further read the photo diodes 5 and 7 to gather measured intensities at the different vertical positions. The microprocessor 11 can further control the pick-and-place unit 10 to cause a vertical movement and a rotation. The microprocessor 11 can further calculate vertical positions of the separating medium 9 and of the serum 2 in response to read measured intensities. The microprocessor 11 can detect the depicted clot 1, as will be described with reference to FIG. 2.

FIG. 2 schematically illustrates a method for detecting the clot 1. FIG. 2 depicts a number of different vertical (irradiating) positions P_0 to P_n. Starting with vertical irradiating position P_0, light generated by the laser diode 4 can be irradiated to the sample container 3 substantially perpendicular to the vertical axis Z of the sample container 3 such that the light can pass through the sample container 3 along a first measurement path R_1 having the vertical irradiating position P_0. A resulting intensity of light passing along the first measurement path R_1 can be measured.

Now the sample container 3 can be rotated around the vertical axis Z for example, about 45 degrees without changing the vertical irradiating position P_0 such that the light irradiated by the first laser diode 4 can pass through the sample container 3 along a second measurement path R_2 being different from the first measurement path R_1. Then, a resulting intensity of light passing along the second measurement path R_2 can be measured.

Optionally, the sample container 3 may be further rotated around the vertical axis Z for example, about −45 degrees with respect to the start angle, again without changing the vertical irradiating position P_0, such that the light irradiated by the first laser diode 4 can pass through the sample container 3 along a third measurement path R_3 being different from the measurement paths R_1 and R_2. Accordingly, a resulting intensity of light passing along the third measurement path R_3 can be measured. Self-evidently, even more than three different measurement paths may be evaluated.

After the intensities corresponding to the measurement paths R1 to R3 have been measured, the microprocessor 11 can compare the measured intensities. If the intensities differ by more than a given quantity, a clot can be detected. Since at the vertical irradiating position P_0 no clot is present, the measured intensities can be basically identical and consequently no clot may be detected.

Now the vertical irradiating position can be changed to vertical irradiating position P_1 and the above described steps can be repeated using the resulting measurement paths R1 to R3. The measurement paths R1 to R3 of the vertical irradiating position P_1 can differ from the measurement paths R1 to R3 of the vertical irradiating position P_0 only in their vertical position. Since at the vertical irradiating position P_1 no clot is present, the measured intensities can again be basically identical and, consequently, no clot may be detected.

Now the vertical irradiating position can be changed to vertical irradiating position P_2 and the above described steps can be repeated using the resulting measurement paths R1 to R3.

As shown in the diagram, depicting the measured intensity of measurement path R2 over the vertical irradiating position, the measured intensity of measurement path R2 can be lowered since the clot 1 may be located within the measurement path R2. Since the clot 1 may not be located within the measurement paths R1 and R3, the corresponding measured intensities can be significantly higher than the measured intensity corresponding to measurement path R2. Thus, by comparing the measured intensities, the clot 1 can be detected.

By changing the vertical irradiating positions, the sample container 3 can at least be partially inserted into a sample container carrier 12. By performing two tasks, namely clot detection and carrier insertion, in parallel, the overall processing time may be reduced.

Clots not exactly symmetric to the vertical axis Z may safely be detected by this method since such clots can cause inhomogeneous measured intensities.

The vertical irradiating position can be changed to final vertical irradiating position P_n which can denote the end vertical position of the serum 2. The end vertical position of the serum 2 may have been determined before.

Under certain circumstances, a clot may also be determined without rotating the sample container 3. If, for example, the vertical interface between the serum 2 and the separating medium 9 has been determined before clot detection, it may be monitored, if for a certain vertical irradiating position within the serum 2 the measured intensity can be below a given threshold and/or can be smaller than measured intensities corresponding to other vertical irradiating position within the serum 2. If this would be the case, a clot can be determined.

Using this method, even clots that are basically symmetric to the vertical axis Z may safely be detected. Further, a number of clots and/or a vertical and horizontal circumference of a clot may be determined.

FIG. 3 schematically illustrates a laboratory automation system comprising the apparatus 100, a centrifuge 15, and an exemplary laboratory station in form of an aliquoter unit 14. The apparatus 100 and the aliquoter unit 14 can be coupled by a conventional data or field bus. The system may also include further laboratory stations such as, for example, pre-analytical stations, analytical stations and post-analytical stations.

The sample containers 3 can be supplied after being centrifuged by the centrifuge 15 or already centrifuged within racks.

The aliquoter unit 14 can transfer part of the serum 2 to one or more secondary tubes (not shown). The aliquoter unit 14 can include a pipetting unit (not shown). The pipetting unit can have a tip (not shown). During aliquoting, the aliquoter unit 14 can control a vertical position of the tip in response to a detected vertical position of an interface between the serum 2 and the separating medium 9 such that the tip can remain within the serum 2 above the separating medium 9.

Further, the aliquoter unit 14 can control aliquoting in response to the clot detection result provided by the apparatus 100 for detecting clots. If a clot 1 is detected, the aliquoter unit 14 may, for example, control the vertical and/or horizontal position of the tip such that the tip may not be blocked or absorbed by the clot 1. Alternatively, a sample container 3 including a clot 1 (or a given number of clots and/or a clot having a dimension bigger than a threshold) may be omitted from further processing.

The system can further include a sample container transport unit to transport sample containers 3 between the apparatus 100, the aliquoter unit 14 and further laboratory stations (not shown). The sample container transport unit can include a number of sample container carriers 12 and a conveyor 13. The sample container carriers 12 can be attached to the conveyor 13.

Figure 4:
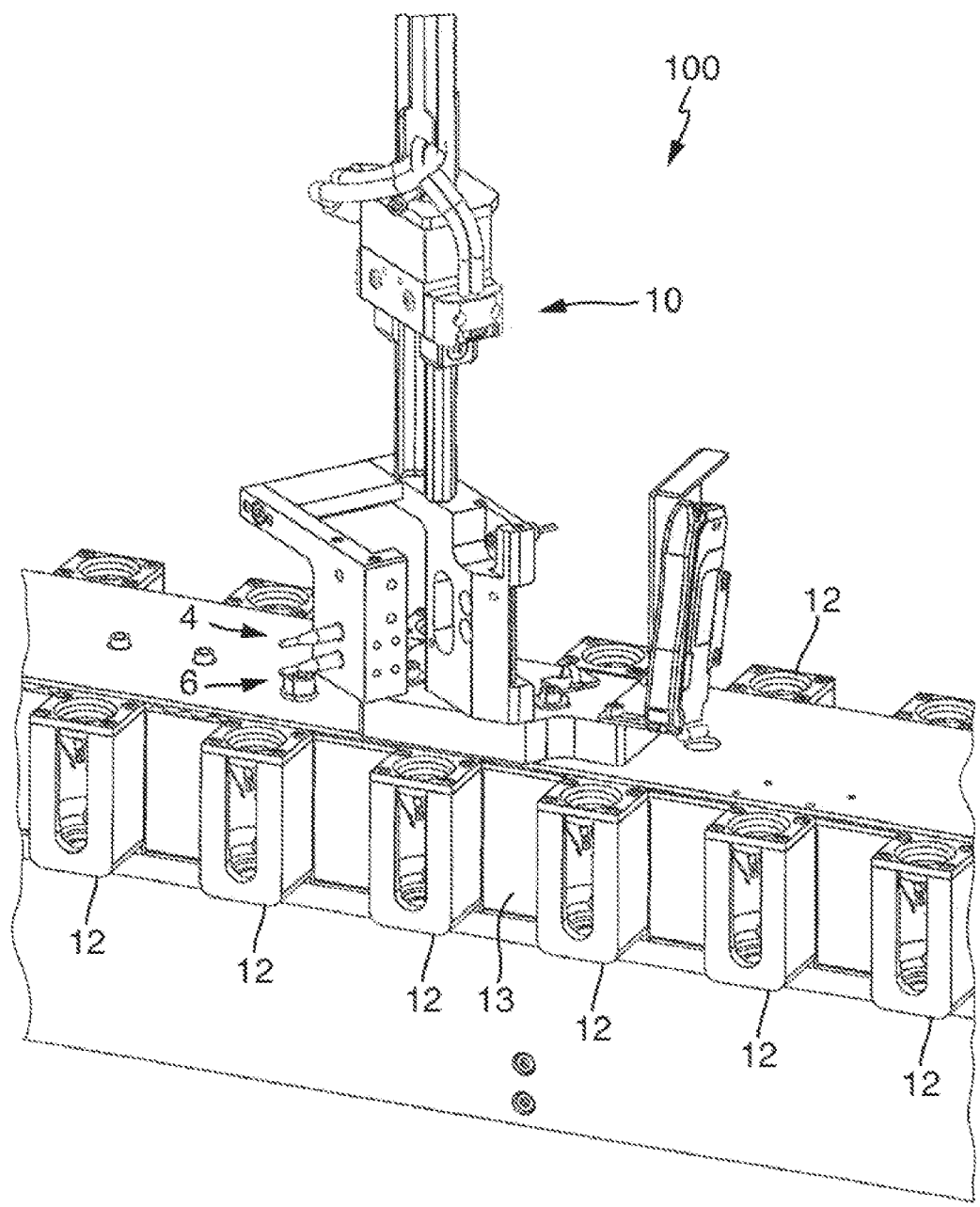
FIG. 4 illustrates schematically the laboratory automation system depicted in FIG. 3 in more detail according to an embodiment of the present disclosure.

FIG. 4 schematically illustrates the driving unit or pick-and-place unit 10 and the sample container transport unit in more detail. The driving unit or pick-and-place unit 10 can include a gripper to grip the sample container 3. The driving unit or pick-and-place unit 10 can further provide a relative motion between the light sources 4 and 6 as well as the measuring units 5 and 7 and the sample container 3 in both a substantially vertical direction aligned with the central axis Z of the cylindrical sample container 3 and in a rotational direction about the central axis Z of the sample container 3.

The driving unit or pick-and-place unit 10 can insert a sample container 3 into a corresponding sample container carrier 12. The apparatus 100 can simultaneously detect the vertical position of an interface and can perform clot detection. During insertion, the conveyor 13 can be stopped. After insertion, the conveyor 13 can be moved such that an empty sample container carrier 12 can be placed under the pick-and-place unit 10 such that a further sample container 3 may be inserted into the empty sample container carrier 12.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for detecting clots in serum, the serum being in a sample container, the sample container comprising a centrifuged blood sample, the blood sample being separated into the serum and at least one other component, the method comprising:

irradiating light having a first wavelength to the sample container by a first light source at a vertical irradiating position such that the light irradiated by the first light source passes through the sample container along a first measurement path;

measuring an intensity of light having the first wavelength passing along the first measurement path and exiting the sample container;

rotating the sample container and/or the first light source around a vertical axis of the sample container without changing the vertical irradiating position such that the light irradiated by the first light source passes through the sample container along a second measurement path being different from the first measurement path;

measuring an intensity of light having the first wavelength passing along the second measurement path and exiting the sample container; and detecting clots in serum in response to the measured intensity corresponding to the first measurement path and the measured intensity corresponding to the second measurement path.

2. The method according to claim 1, wherein clots are detected for a given vertical irradiating position if the measured intensity corresponding to the first measurement path differs from the measured intensity corresponding to the second measurement path by more than a given quantity.

3. The method according to claim 1, wherein when moving the sample container relative to the first light source, the sample container and/or the first light source are rotated around a vertical axis of the sample container.

4. The method according to claim 1, wherein the first wavelength ranges from 400 nm to 1200 nm.

5. The method according to claim 1, further comprising, changing the vertical irradiating position.

6. The method according to claim 5, wherein repeat the irradiation of light and the measurement of the intensity of light having the first wavelength at the changed vertical irradiating position.

7. The method according to claim 5, wherein the detection of clots further comprises detecting clots in response to the measured intensities corresponding to the first measurement paths having different vertical irradiating positions.

8. The method according to claim 5, wherein by changing the vertical irradiating position, the sample container is inserted into a sample container carrier.

9. The method according to claim 1, further comprising, irradiating light to the sample container having a second wavelength at different vertical irradiating positions;

measuring an intensity of light having the second wavelength exiting the sample container at the different vertical irradiating positions; and calculating vertical positions of the separating medium and of the at least one other component in response to the measured intensities corresponding to the second wavelength and the measured intensities corresponding to the first wavelength.

10. The method according to claim 9, wherein the second wavelength ranges from 1300 nm to 1700 nm.

11. An apparatus to perform a method according to claim 1, the apparatus comprising:

the first light source;

a first measuring unit to measure an intensity of light having the first wavelength and exiting the sample container; and a computing unit to detect clots in response to the measured intensities.

12. The apparatus according to claim 11, further comprising, a driving unit for moving the sample container relative to the first light source.

13. The apparatus according to claim 11, wherein the sample container comprises a centrifuged blood sample, the blood sample being separated into serum and at least one other component, wherein the serum forms the liquid, the apparatus further comprising, a second light source to irradiate light having the second wavelength to the sample container at different vertical irradiating positions; and a second measuring unit to measure an intensity of light having the second wavelength and exiting the sample container, wherein the computing unit calculates positions of the separating medium and of the at least one other component in response to the measured intensities corresponding to the second wavelength and the measured intensities corresponding to the first wavelength.

14. A laboratory automation system for processing components comprised in a sample container, the system comprising:

the apparatus according to claim 11, and at least one aliquoter unit coupled to the apparatus, wherein the aliquoter unit performs aliquoting in response to the clot detection.

* * * * *